United States Patent [19]
Hirabayashi

[11] Patent Number: 5,329,276
[45] Date of Patent: Jul. 12, 1994

[54] MULTIDIMENSIONAL SIGNAL INPUT DEVICE

[75] Inventor: Tsukamitsu Hirabayashi, Iruma, Japan

[73] Assignee: Kabushiki Kaisha Yaskawa Denki, Fukuoka, Japan

[21] Appl. No.: 867,091

[22] PCT Filed: Dec. 19, 1990

[86] PCT No.: PCT/JP91/01735

§ 371 Date: Jun. 29, 1992

§ 102(e) Date: Jun. 29, 1992

[87] PCT Pub. No.: WO92/11594

PCT Pub. Date: Jul. 9, 1992

[30] Foreign Application Priority Data

Dec. 19, 1990 [JP] Japan ................................ 2-412300

[51] Int. Cl.$^5$ .......................... G08C 19/06; G09G 3/02
[52] U.S. Cl. .............................. 340/870.31; 341/20; 273/438; 364/190; 345/157; 345/161
[58] Field of Search ............ 340/870.31, 709, 710, 340/671; 273/438; 341/23, 29, 31-34, 20; 345/145, 157, 161, 167, 164, 162, 160, 159; 364/190

[56] References Cited

U.S. PATENT DOCUMENTS

| | | | |
|---|---|---|---|
| 4,563,740 | 1/1986 | Blake et al. | 340/709 |
| 4,787,051 | 11/1988 | Olson | 340/710 |
| 4,839,838 | 6/1989 | LaBiche et al. | 340/710 |
| 5,128,671 | 7/1992 | Thomas, Jr. | 340/709 |
| 5,223,709 | 6/1993 | Pettypiece, Jr. | 340/709 |

FOREIGN PATENT DOCUMENTS

| | | |
|---|---|---|
| 59-61708 | 4/1984 | Japan . |
| 62-40519 | 2/1987 | Japan . |
| 64-28720 | 1/1989 | Japan . |
| 1-96720 | 4/1989 | Japan . |

*Primary Examiner*—Donnie L. Crosland
*Attorney, Agent, or Firm*—Jordan and Hamburg

[57] ABSTRACT

A device is provided which allows multidimensional information signals concerning coordinates, directions and the like of an object to be input to a CPU exactly as intended by an operator on a non-contact basis, and without restrictions on the place where it is used. Angular velocity detectors (4), (5), and (6) are provided on the X-axis, Y-axis, and Z-axis, orthogonal to each other of an operation unit which is shaped to be easily gripped by an operator or to be mounted on an articulation, shoulder, or head. The operation unit (1) is rotated and moved and, when the operator wishes to input information, push-buttons (2) and (3) provided on the operation unit (1) are turned on/off to command the start or stop of the counting of the output of the angular velocity detectors (4), (5), and (6). In response to the command, the angular velocity signals of the axes are converted into information to be input to the CPU through V/F converters, pulse conversion circuits, gate circuits, and counter circuits. The motion of an operator can be commanded as the operator intends in arbitrary space, thereby facilitating the movement of a robot arm and the rotation and movement on a display screen of a three-dimensional CAD system or graphic system. In addition, a person who has a handicap in his or her hand or leg can operate and issue commands.

6 Claims, 4 Drawing Sheets

MULTIDIMENSIONAL SIGNAL INPUT DEVICE

FIELD OF ART

The present invention is a multidimensional signal input device which is suitable for use as a device by which an operator gives relative motion commands on a non-contact basis while observing an object to be controlled to convert intended information into electric signals, and which is especially suitable for use as a device for inputting two-dimensional or three-dimensional coordinates or directions for a computer or an operation command device for a robot.

BACKGROUND OF THE INVENTION

Ordinarily, a track ball, a joy stick, a mouse or the like have been widely used as devices for inputting coordinates or directions for a computer.

However, in the case of a conventional mouse, as a ball in the mouse is rolled and the quantity of the displacement is mechanically detected, it requires a certain range of smooth surface to be operated.

Although a conventional joy stick does not occupy much space, its movable portion has a limited range, which makes it difficult to use for performing minute input operations.

A conventional track ball does not have the problems as described above but it is difficult to operate the buttons on the track ball and the track ball itself simultaneously.

Further, though these devices are intrinsically two-dimensional dimensional input devices, there are conventional devices which have been modified into three-dimensional input devices (refer to unexamined Japanese published patent application No. 62-40619 for a track ball which represents such a case). However, since these three-dimensional devices are obtained by modifying intrinsically two-dimensional devices, they require the operator to perform unnatural operations that are different from what the operator intends.

As a device for three-dimensional input operations on a non-contact basis, for example, unexamined Japanese published patent application No. 1-96720 discloses a coordinate input device utilizing an acceleration sensor. When this device is manually put in a translation motion, it detects the motion from the acceleration. It does not provide information regarding rotation and is apt to generate operational errors, and it is expensive because it performs complicated operations wherein the acceleration must be integrated twice to be converted into position coordinates.

It is an object of the present invention to provide a non-contact multidimensional information input device which solves the above-mentioned problems and allows input to be made in a way that the operator intends with high accuracy at low cost and without restrictions on the place in which it is used.

DISCLOSURE OF THE INVENTION

In order to accomplish such purposes, the present invention comprises angular velocity detectors provided on the X-axis, Y-axis, and Z-axis which are orthogonal to each other, an operation unit in which said angular velocity detectors are installed, a shape like a box or an elliptic cylinder with grooves provided at the side portion thereof which comes into contact with three fingers, for facilitating gripping and installation on an articulation, shoulder, head or the like, and a circuit which converts angular velocity signals of each axis obtained from the operation unit into signals usable by a computer by means of V/F converters, sign detection circuits connected in parallel with the V/F converters, gate circuits for counting or stopping the output of the V/F converters in response to a command signal from a button pushed by an operator, and counter circuits. The motion of the operator's hand is directly detected by the operation unit. Output signals from the operation unit are processed and input to a computer as displacement signals, and commands from the operator are given through button operations.

When the operator maneuvers the operation unit into a three-dimensional rotary motion, the angular velocity detectors provided on the axes detect angular velocities about the X-axis, Y-axis and Z-axis. The angular velocities are integrated once by the circuit from the V/F converters up to the counter circuits to obtain three-dimensional displacement.

According to the present invention, the motion of the operator is directly converted into electric signals. Therefore, the motion of the operator can be input as it is. Further, the motion of the operator is directly used as a relative motion command input according to the present invention. This feature makes the operation quite easy in CAD systems handling three-dimensional objects in arbitrary spaces on a non-contact basis, in inputting three-dimensional directions in graphic systems, and in cursor control in computers.

In addition, buttons or the like may be provided on the operation unit for information-signal input mode switching that allows information on translation motions and rotary motions to be input.

While the conventional computer input devices have been manually operated, the present invention allows input operations with a device mounted on any one of a plurality of articulations, such as a head or shoulder, that are free to move.

DESCRIPTION OF THE PREFERRED EMBODIMENT

An embodiment of the present invention will now be described with reference to FIG. 1 and FIG. 2.

Figure 1:
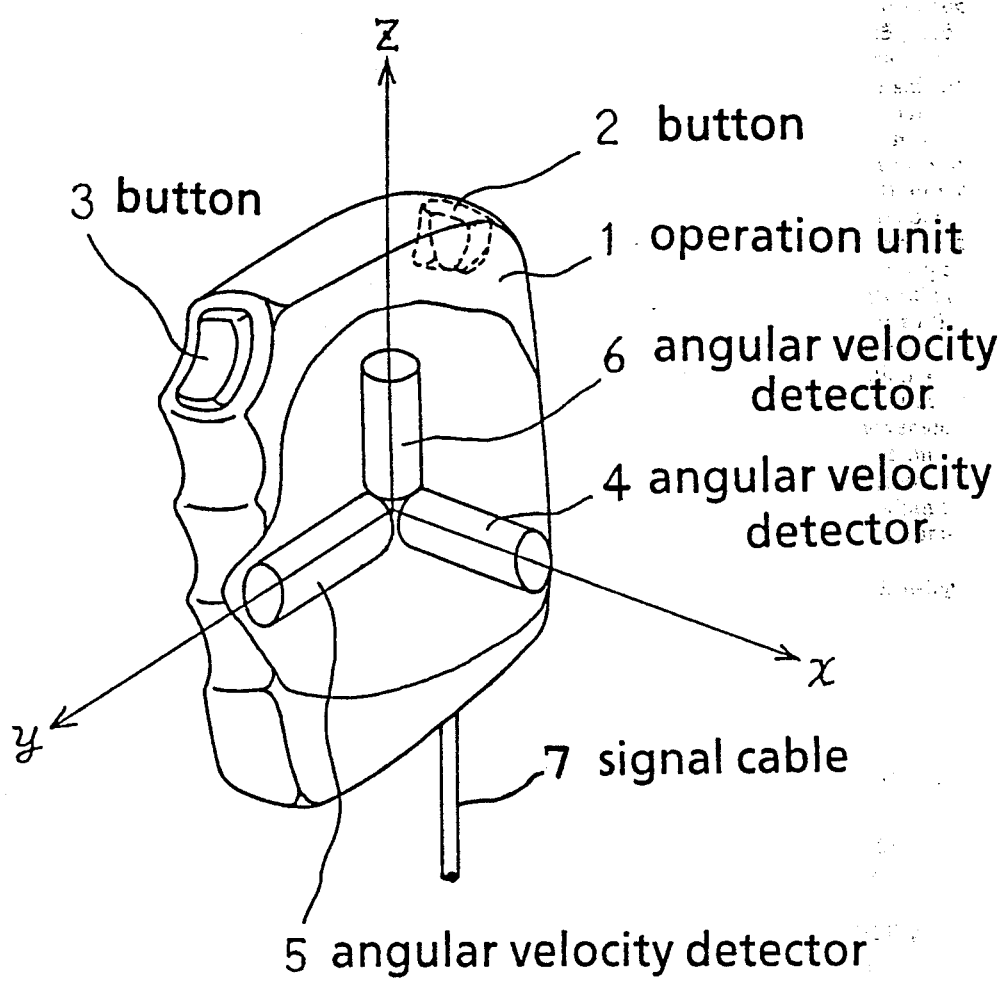
FIG. 1 is a perspective view, partially in section, showing an embodiment of an information input device of the present invention.

In FIG. 1, angular velocity detectors 4, 5 and 6 on the X-axis, Y-axis and Z-axis, respectively, which are orthogonal to each other, are incorporated in an operation unit which is formed in a shape like a box or an elliptic cylinder as a whole, with elliptic grooves at the side portion thereof which come into contact with three fingers for providing a better fit when gripped.

According to the present invention, tuning fork-type gyroscopes act as the angular velocity detectors.

They output voltages in proportion to angular velocities when rotary displacement is made about an axis in parallel with a vibrator of the tuning fork type. Of course, the angular velocity detectors are not limited to tuning fork type gyroscopes.

Operation buttons 2 and 3, with which an operator inputs instructions, are provided at a position on the outer surface of the upper part of the operation unit 1 which fits a thumb and forefinger.

An operator grips this unit and induces the rotary displacement. Then, angular velocities of rotary motions about those axes are detected by the respective angular velocity detectors 4, 5, and 6.

Figure 2:
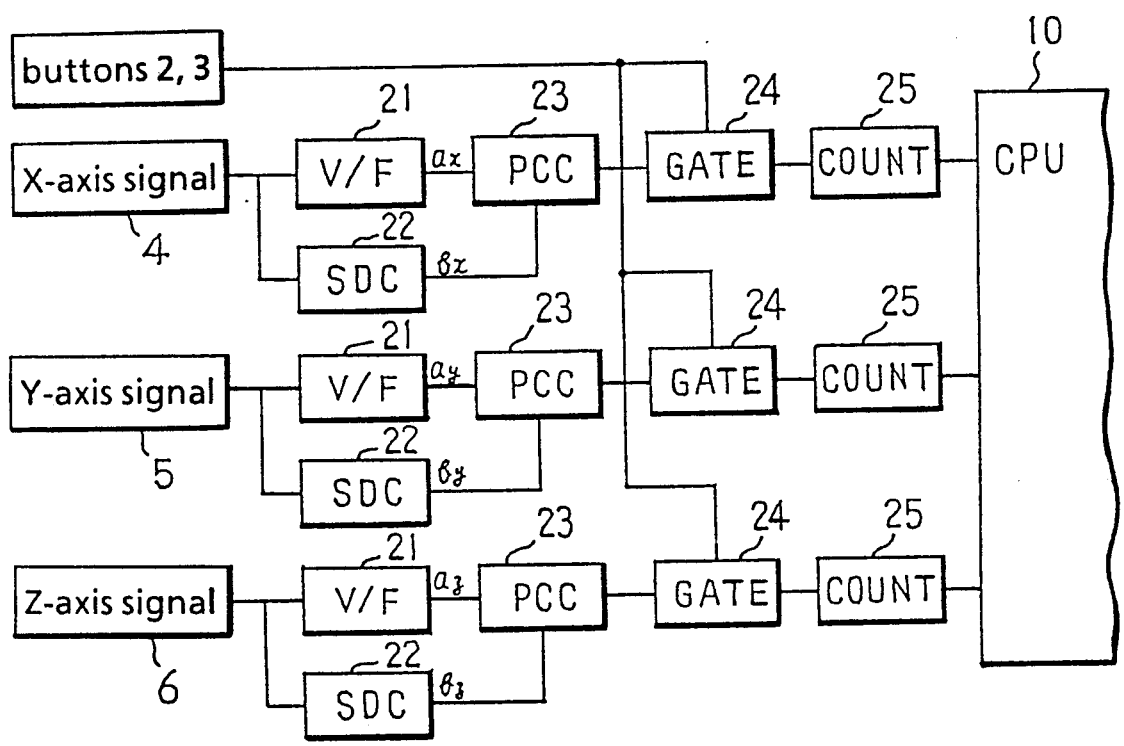
FIG. 2 is a block diagram of a control circuit.

Output signals, i.e., an X-axis signal, Y-axis signal, and Z-axis signal of the angular velocity detectors 4, 5, and 6, respectively, are input through a signal cable 7 to voltage-to-frequency conversion circuits 21, 21, and 21 shown in FIG. 2 and sign detection circuits 22, 22, and 22 for determining whether the direction of rotation is positive or negative, and connected in parallel with the conversion circuits.

The output of the voltage-to-frequency conversion circuits 21, 21, and 21 and sign detection circuits 22, 22 and 22 are input to pulse conversion circuits 23, 23, and 23, respectively.

Figure 3:
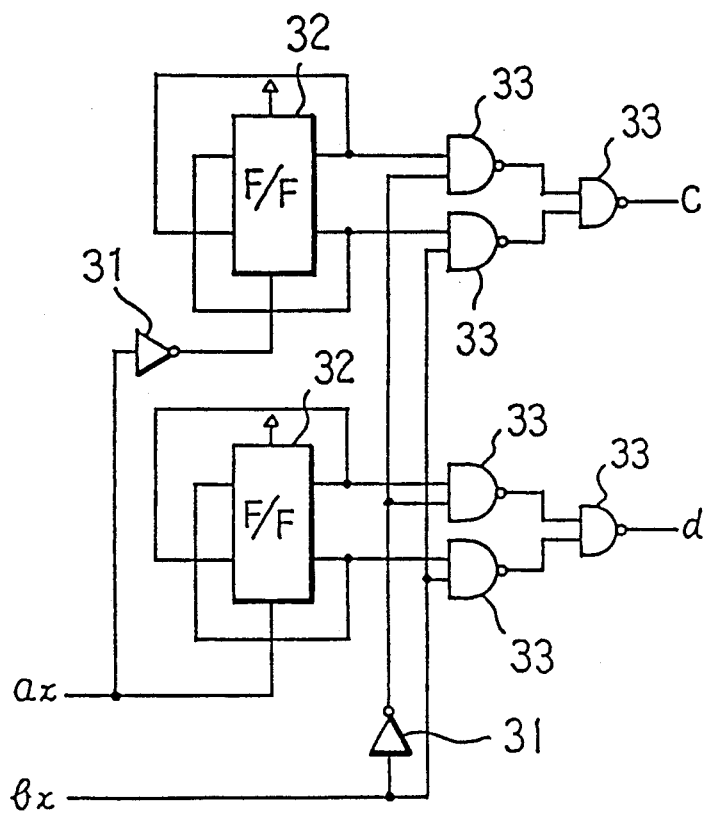
FIG. 3 is a block diagram of a pulse conversion circuit.
Figure 4:
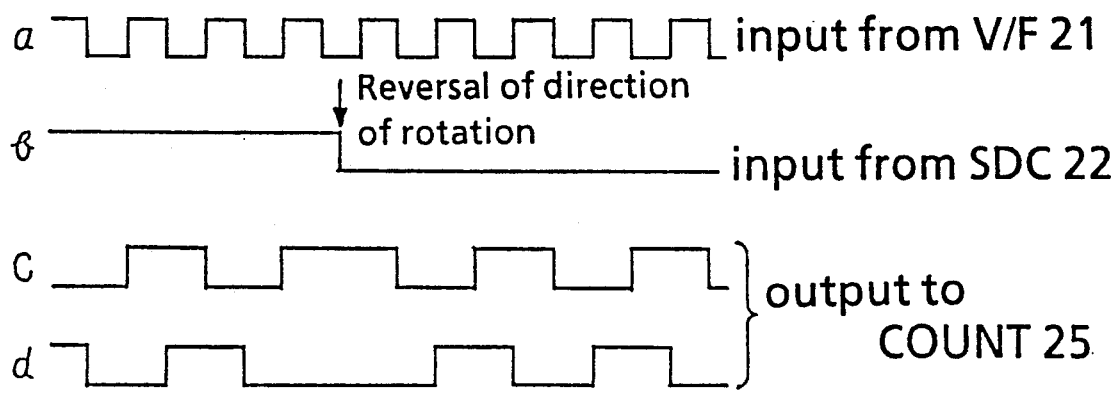
FIG. 4 is a timing chart for the pulse conversion circuit.

Each of the pulse conversion circuits may be constituted by a gate circuit comprising two flip-flops 32, two sign converters 31, and six NAND gates 33, as illustrated in FIG. 3, for one axis. When an output $a_x$ of a voltage-to-frequency conversion circuit 21 and an output $b_x$ of a sign detection circuit 22 are input to this circuit at the timing shown in FIG. 4, i.e., two phase-shifted pulses, an A-phase pulse c and B-phase pulse d which are equivalent to the output signals obtained from an optical encoder are output.

The output of the axes of the pulse conversion circuits 23, 23, and 23 is input to output gate circuits 24, 24, and 24. The operator inputs, with the operation buttons 2 and 3, command signals for commanding input timing to the gate circuits 24, 24, and 24 to control the timing of the output from the pulse conversion circuits 23, 23, and 23.

The output of the gate circuits 24, 24, and 24 is input to counter circuits 25, 25, and 25 which add the number of pulses corresponding to the commanded timing, allowing the quantity of a relative motion to be commanded to an object to be controlled.

If the output of the counter circuits 25, 25, and 25 is directly used as information input to a computer 10, it constitutes a rotation command in a graphic screen.

Figure 5:
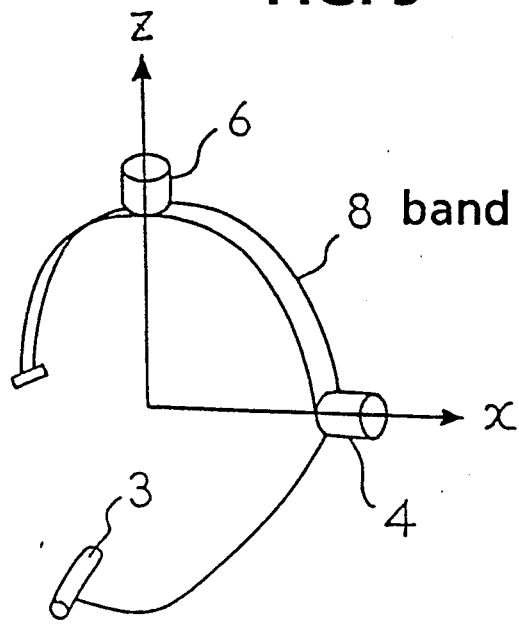
FIG. 5 is a perspective view showing another embodiment.

In another embodiment shown in FIG. 5, as the operation unit, angular velocity detectors 4 and 6 serving only two axes, i.e., X-axis and Z-axis, are provided so that they cross the band of a headphone at right angles. In this case, control circuits are required for only two axes. An operator wears the unit and shakes his or her head. Thus, the unit can be used as an input device which replaces a conventional mouse.

It is possible to use a helmet instead of a headphone. In this case, the angular velocity detectors 4, 5 and 6 may be provided in crossed position.

Figure 6:
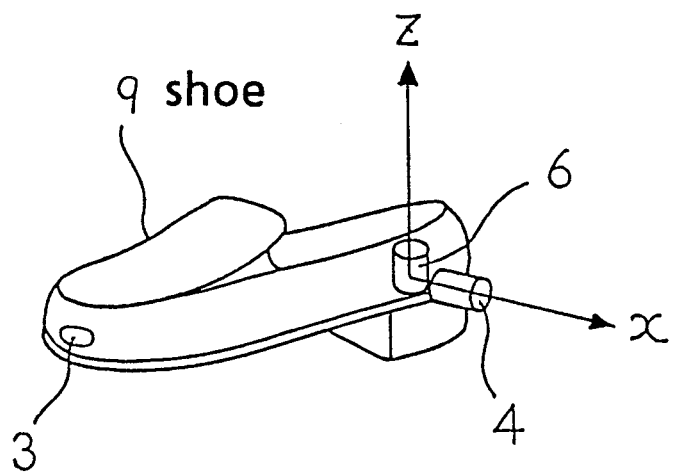
FIG. 6 is a perspective view showing another embodiment.

In still another embodiment shown in FIG. 6, the operation unit has a shoe-shaped configuration wherein the angular velocity detectors are disposed in the same way as in other embodiments; and an operation button 3 is provided at the part corresponding to the big toe. This allows the motions of a foot and big toe of an operator to be directly input. In this case, however, unnecessary motions of the operator may be input. In order to avoid this, the operation unit 1 as shown in the embodiment (FIG. 1) may be used, in addition, to issue a command after checking the validity of a displacement detection signal with the button 2.

Thus, the present device can be used by a person who has a handicap with his or her hand as a cursor control device for a computer display.

The present invention can be utilized in a multidimensional signal input device to be used as a device for inputting two-dimensional or three-dimensional coordinates, or directions for a computer, or as an operation command device for a robot.

I claim:

1. A multidimensional signal input device comprising:
an operation unit including:
a plurality of angular velocity detector means, on orthogonal axes, each for detecting an angular velocity of said operation unit, and
operation buttons on an outer surface thereof,
voltage-to-frequency converter means, connected to outputs of said angular velocity detector means, each for producing a converted output,
sign detection circuits connected in parallel with said voltage-to-frequency converter means, each for determining a direction of said angular velocity,
gate circuit means for validating or invalidating a count of converted outputs of said voltage-to-frequency converter means in response to a command timing from said operation buttons, and
counter circuit means, connected to said gate circuit means, for producing a count output corresponding to said command timing and supplying said count output to a control device for producing movement in response thereto.

2. A multidimensional signal input device according to claim 1 wherein said angular velocity detector means are disposed on three orthogonal axes.

3. A multidimensional signal input device according to claim 1 wherein said angular velocity detector means are disposed on two orthogonal axes.

4. A multidimensional signal input device according to claim 1, 2, or 3 wherein said operation unit has a shape like an elliptic cylinder, having elliptic grooves at a portion thereof which comes into contact with three fingers of a hand, enabling said operation unit to be easily gripped.

5. A multidimensional signal input device according to claim 1, 2, or 3 wherein said operation unit has a shape like a shoe.

6. A multidimensional signal input device according to claim 1, 2, or 3 wherein said operation unit has a shape like a headphone.

* * * * *